United States Patent [19]

Dunski et al.

[11] Patent Number: 4,990,671
[45] Date of Patent: Feb. 5, 1991

[54] METHOD FOR MAKING AMINOPHENOLS AND THEIR AMIDE DERIVATIVES

[75] Inventors: Neil Dunski, St. Louis County; Henry J. Buehler, Affton, both of Mo.

[73] Assignee: Mallinckrodt, Inc., St. Louis, Mo.

[21] Appl. No.: 449,240

[22] Filed: Dec. 7, 1989

Related U.S. Application Data

[62] Division of Ser. No. 182,533, Apr. 18, 1988, abandoned.

[51] Int. Cl.$^5$ .................... C07C 231/02; C07C 209.38
[52] U.S. Cl. ..................................... 564/418; 564/143; 564/144
[58] Field of Search ............... 564/411, 418, 420, 421, 564/422, 423, 143, 144

[56] References Cited

U.S. PATENT DOCUMENTS

| | | | |
|---|---|---|---|
| 1,978,433 | 10/1934 | Major | 260/128 |
| 3,845,129 | 10/1974 | Reid | 564/418 X |
| 3,978,131 | 8/1976 | Pawellek et al. | 564/422 |
| 4,152,319 | 5/1979 | Kline | 564/207 X |
| 4,205,151 | 5/1980 | Dale et al. | 526/262 |
| 4,658,054 | 4/1987 | Conley | 564/142 X |

FOREIGN PATENT DOCUMENTS

| | | | |
|---|---|---|---|
| 1417451 | 11/1964 | France. | |
| 1432356 | 5/1965 | France. | |
| 2533559 | 9/1982 | France. | |
| 1241066 | 7/1971 | United Kingdom | 564/420 |

OTHER PUBLICATIONS

Fieser et al., "Synthetic Organic Reagents", vol. 1, pp. 1109–1110 (1967).
Geigy, "Chemical Abstracts", vol. 62, p. 11834d (1965).
ICI, "Chemical Abstracts", vol. 64, p. 12602 (1966).

*Primary Examiner*—Richard L. Raymond

[57] ABSTRACT

N-acylated dialkylaminophenols are produced at greater yields under mild reaction conditions by a novel in situ process which begins with catalytic hydrogenation of dialkylnitrosophenols in an aprotic organic reaction medium.

8 Claims, No Drawings

METHOD FOR MAKING AMINOPHENOLS AND THEIR AMIDE DERIVATIVES

This is a division of application Ser. No. 182,533, filed Apr. 18, 1988, now abandoned.

BACKGROUND OF THE INVENTION

This invention relates to the production of aminophenols and their N-acylated amide derivatives which are ordinarily used as polymeric stabilizers or anti-oxidants. More particularly, this invention relates to the production of these anti-oxidant compounds under mild catalytic hydrogenation reaction conditions, where severe losses in product yield have been experienced in the past.

N-acylated aminophenols are known to be useful as anti-oxidants in many different compositions, such as rubbers, resins and other materials which are subject to the deleterious effects of oxidative aging.

These compounds are generally prepared by nitrosation or nitration of a phenol, followed by reduction of the nitroso-group or nitro-group to the corresponding amine, and subsequently N-acylating the amine.

Although it has been known for quite some time that the reduction step of the process may be accomplished by catalytic hydrogenation under pressure, the normal practice has continued to involve chemical reduction of the nitro or nitroso groups with, for example, sodium hydrosulfite or sodium bisulfite such as the method disclosed in Netherlands Patent Application 6,505,775 (Chemical Abstracts Vol. 64, No. 12601d, 1966), because of poor yields, long reaction times, and relatively severe operating conditions, including excessively high temperatures and pressures. Additionally, the catalytic hydrogenation requires a cumbersome isolation of the intermediate from its reaction medium prior to acylation.

For example, as recently as 1979, R. H. Kline disclosed in his U.S. Pat. No. 4,152,319, Example 2, a two-step process for preparing the anti-oxidant N-(3,5-di-tert-butyl-4 hydroxyphenyl) methacrylamide including catalytic hydrogenation. In the first step, 23.5 grams of the nitrosophenol precursor was catalytically hydrogenated to produce the aminophenol at 50 psi and 50° C. in a reaction medium of absolute ethanol over a period of one hour. In the second step, after isolating the aminophenol solution, the acid chloride, methacryloyl chloride dissolved in benzene, was reacted to produce the N-acylated aminophenol. However, the yield of 10 grams of product was only 35% of theoretical.

Later, in 1980, Mr. J. A. Dale disclosed in his U.S. Pat. No. 4,205,151, improved yields from the catalytic hydrogenation of nitrophenols in tetrahydrofuran at relatively short reaction times (15–20 hours) but at quite severe pressures and temperatures of between 50° and 150° C., and from 100 psi to about 1500 psi and very low concentrations. However, the hydrogenation required about 20 hours at milder operating conditions such as 100 psi and 50° C. While Dale disclosed conducting the catalytic hydrogenation in an aprotic solvent such as tetrahydrofuran, poor results were achieved. Although Dale does disclose the prospect of augmenting his reaction medium with certain non-polar organic substituents, such as toluene, benzene and hexane, he demonstrates that the reaction cannot proceed in those solvents alone. For example, hexane alone as a reaction medium presented difficulty and therefore the tetrahydrofuran was employed. Even then, however, as explained in Dale's Example 2, when the hydrogenation was conducted at 50 psi and presumably room temperature, despite conducting the reaction for four days, he could achieve only a 50% conversion. Thereafter, Mr. Dale discloses that by carrying out the hydrogenation reaction in tetrahydrofuran (eliminating the hexane), increasing the pressure to 1,000 psi, and raising the temperature to 85° C., he could achieve a 100% yield, and that at 80° C. over 15 hours, under pressure of at least 200 psi, he obtained 100% yield.

Accordingly, a method for manufacturing N-acylated aminophenols beginning with catalytic hydrogenation at milder operating conditions, shorter reaction times, and yet having commercially acceptable yields, would be a substantial advancement in the art.

SUMMARY OF THE INVENTION

It is a principle object of the present invention to provide a novel method for making N-acylated aminophenols under mild catalytic hydrogenation operating conditions, and without isolating the amine intermediate.

It is a further object of the present invention to provide a novel method of making aminophenols at high yields by catalytic hydrogenation having reduced reaction time without proportional increases in either temperature or pressure.

It is a still further object of the present invention to provide a novel method of N-acylated aminophenols at short reaction times, under mild operating conditions, and producing higher product yields without isolating the aminophenol intermediate from the catalytic hydrogenation and without using a separate reaction mediums for the hydrogenation and the acylation.

These objects and others will become more readily apparent from the following detailed description and the examples. The objects are fulfilled by novel formation of N-acylated aminophenol wherein the catalytic hydrogenation and the acylation are conducted in an aprotic organic solvent in situ.

DETAILED DESCRIPTION AND PREFERRED EMBODIMENTS

In accordance with the present invention, the reduction of 2,6-dialkyl-4-nitrosophenol to its corresponding aminophenol and the subsequent acylation are carried out in situ. Both reactions are conducted in a single aprotic organic reaction medium.

The aprotic organic solvents which form the in situ reaction medium of the present invention are aprotic organic liquids having at least the affinity for solubilizing small amounts of nitrosophenol as does hexane at room temperature or slightly above and which are inert to the acylation reaction. Said solvents may be, for example, chlorinated hydrocarbons, such as chloroform and dichloromethane; aromatics, such as toluene or benzene; aliphatic hydrocarbons, such as hexane; and aprotic amides, such as N,N-dimethylformamide.

Although it has been known since at least as early as 1957 from W. J. Croxall's U.S. Pat. No. 2,799,692, that the N-acylation reaction between, for example, an acid and an aminophenol can be carried out in aprotic solvents such as benzene, xylene and toluene to remove the water as formed, no one until now has tried the catalytic hydrogenation followed by an N-acylation reaction in such a solvent other than the recent attempt by J. A. Dale. In his U.S. Pat. No. 4,205,151, J. A. Dale unsuccessfully attempted such hydrogenation in the aprotic solvent, hexane. However, high yields from catalytic hydrogenation were not achieved until completely eliminating hexane in the reaction medium and substantially increasing the temperature and pressure. The failure of others to expeditiously investigate the use of aprotic solvents particularly non-polar types as a means of improving the catalytic hydrogenation and forming the N-acylated aminophenol in situ may have been due in part to their awareness of Dale's low yields absent long reaction times and excessively high pressures and temperatures, even when employing aprotic solvents such as tetrahydrofuran. hydrogenation.

Although R. H. Kline, in his U.S. Pat. No. 4,152,319, disclosed the use of aprotic solvents such as benzene for the second step of his process, i.e. the acylation step, his preceding catalytic hydrogenation was conducted in absolute ethanol which is a polar protic solvent.

Although the success of the present invention is not completely understood, one possible reason is that we have for the first time discovered a distinction between the hydrogenation of nitrosophenols and that of nitrophenols, i.e. aprotic solvents serve to promote the catalytic hydrogenation of nitrosophenols thus permitting acylation in the same reaction medium, while such solvents alone serve to inhibit catalytic hydrogenation for nitrophenols.

In the process of the present invention, the in situ process is conducted in aprotic solvents preferably toluene, N,N-dimethylformamide, hexane, dichloromethane, and mixtures thereof. It is critical in employing the process of this invention that the starting material should be a nitrosophenol rather than a nitrophenol.

It is particularly preferred in the process of this invention to employ either N,N-dimethylformamide, hexane, or a mixture of hexane and dichloromethane because these solvents allow one to run these reactions at high concentrations of reactants and because these solvents are highly inert with regard to the reactions taking place. The preferred mixture of hexane and dichloromethane have a volume-to-volume ratio of 1.3 to 1.0 respectively. High yields, relatively low material costs, and high solubility are experienced without the need for highly polar protic solvents such as methanol or ethanol normally used in these reactions, and little plugging of transfer lines during manufacture and filtration of the product is experienced with such solvents.

In the course of this invention, it is preferred to catalytically hydrogenate 2,6-dialkyl-4-nitroso phenols in effective amounts of the above-described reaction medium. The aprotic organic solvents forming the reaction medium serve to solubilize all the reaction product without resorting to high temperatures. The amount of solvent utilized can be measured to maximize the amount of product produced per batch. A particularly preferred 2,6-dialkyl-4-nitroso phenol has the formula:

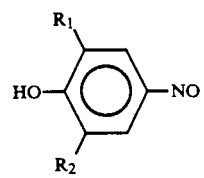

wherein $R_1$ is tert-butyl and $R_2$ is tert-butyl, and is referred to as 2,6-di-tert-butyl-4-nitrosophenol.

The 2,6-dialkyl-4-nitroso phenols, although readily available may be prepared by well-known nitrosation processes.

The catalytic hydrogenation is conducted by contacting a mixture of the nitroso phenol and an aprotic organic solvent such as previously described with a metallic catalyst at a relatively low pressure in the presence of hydrogen gas. The catalyst is preferably an insoluble particulate metallic material. For example, metal or metal oxides such as nickel, nickel oxides, chromium, cobalt, or noble metals such as platinum and palladium. But it is particularly preferred to employ noble metals such as platinum and palladium on an inert support such as carbon. Hydrogenation temperatures are at room temperature, preferably from about 20° to about 50° C. In a particularly preferred embodiment of the present invention, the initial temperature is 23° C. and the exotherm is controlled so that the reaction temperature does not exceed 40° C. for substantially complete conversion at greater than 90% in a reaction period of less than an hour. The positive pressure for hydrogen ranges from about 50 to about 60 psi. In a particularly preferred embodiment of the present invention, the hydrogenation under such pressures at the above-described preferred temperatures results in substantially complete hydrogenation within 30 minutes, although stirring of the mixture under the hydrogen atmosphere can be maintained for a total of one hour if desired.

The in situ process is completed by adding the N-acylating agent. It is particularly preferred to employ acid chlorides such as stearoyl chloride, lauroyl chloride, acetyl chloride or acryloyl chloride. Additionally, acylation may be completed by the use of acetic anhydride or other materials such as hexanoic anhydride, Lauric anhydride or Stearic anhydride. The N-acylating agent is added directly to the reaction medium in substantially stoichiometric amounts, although it may be desirable to employ a slight molar excess of from 1.0 to 10.0 percent. Also, a substituent such as triethyl amine, sodium carbonate or pyridine which works to effectively tie up hydrochloric acid produced during the acylation step. Such substituents are added in molar equivalent to the acid chloride used. It is also preferred to continue to conduct the in situ reaction at this acylation stage under an oxygen-free environment with for example nitrogen. We have found that the acylation yield is substantially enhanced by the exclusion of protic organic solvents. Although hydrogenation of nitrosophenol proceeds very rapidly when protic solvents such as ethanol or methanol are used, the acylation reaction is adversely impacted because the acylating agent reacts with any residual protic solvent producing undesirable by-products such as ethyl or methyl esters and low yields of the desired amide produce.

The following examples are intended for illustrative purposes and not to necessarily limit the invention, although additional objectives and advantages of the invention will become apparent from these illustrations.

EXAMPLE 1

Preparation of N(4-hydroxy-3,5-di-tert-butylphenyl) stearamide

A 2 liter Parr bomb was charged with 23.50 g (0.1 mole) 2,6-di-tert-butyl-4-nitrosophenol, 1.0 g of 5% Pd on C catalyst and 600 ml toluene. After purging the assembled bomb with nitrogen, it was pressurized to 50 psi with hydrogen. The mixture was stirred vigorously and uptake of hydrogen was noted. The hydrogenation step producing 2,6-di-tert-butyl-4-aminophenol was completed within 15 minutes. A temperature rise from 23° C. to 25° C. was observed during the hydrogenation. The mixture was allowed to stir under hydrogen atmosphere for a total of 1 hour.

The system was purged with nitrogen and 9.1 g (0.115 mole) of nitrogen purged pyridine was added to the mixture in the Parr bomb under nitrogen pressure. To the stirred mixture was then added under nitrogen pressure 34.79 g (0.115 mole) nitrogen purged stearoyl chloride. The mixture was allowed to stir in the bomb for one hour under nitrogen atmosphere.

Insoluble catalyst and pyridine hydrochloride were removed by filtration and the toluene stripped off under reduced pressure. The residue was crystallized from methanol yielding 44.3 g (91% yield) of N(4-hydroxy-3,5-di-tert-butylphenyl) stearamide m.p. 97.5°–98.5° C.

EXAMPLE 2

Preparation of N(4-hydroxy-3,5-di-tert-butylphenyl) stearamide

A 2 liter Parr bomb was charged with 11.75 g (0.05 mole) 2,6-di-tert-butyl-4-nitrosophenol, 0.5 g of 5% Pd/C catalyst and 600 ml hexane. In the manner described in Example 1 the material was hydrogenated to 2,6-di-tert-butyl-4-aminophenol. Nitrogen purged solution of 15.89 g (0.15 mole) sodium carbonate in 50 ml water was added to the bomb followed by 16.29 g (0.054 mole) nitrogen purged stearoyl chloride. The mixture was stirred for 2 hours.

Distilled water, 135 ml, was added and the organic layer separated. It was then filtered to remove residual catalyst. The hexane solution was cooled and N(4-hydroxy-3,5-di-tert-butylphenyl) stearamide crystallized out. First crop yield was 17.5 g (72%).

EXAMPLE 3

Preparation of N(4-hydroxy-3,5-di-tert-butylphenyl) stearamide

A 2 liter Parr bomb was charged with 23.5 g (0.1 mole) 2,6-di-tert-butyl-4-nitrosophenol, 0.5 g of 5% Pd/C catalyst and 600 ml DMF (N,N-dimethylformamide). In the manner described in Example 1 the material was hydrogenated to 2,6-di-tert-butyl-4-aminophenol.

The solution was transferred under nitrogen pressure to a nitrogen purged 2 liter round bottom flask. The catalyst was removed on a glass sintered funnel placed between the bomb and the round bottom flask. Nitrogen purged triethylamine, 10.12 g (0.1 mole), was added to the DMF solution followed by slow addition of 30.3 g (0.1 mole) nitrogen purged stearoyl chloride.

After stirring for 2 hours the DMF solution was added to 2 liters of water containing a few cc of $H_2SO_4$. The product precipitated out of solution and was collected by filtration. It was washed with water and hexane and dried overnight. A total of 42.3 g (87%) was obtained.

EXAMPLE 4

Preparation of N(4-hydroxy-3,5-di-tert-butylphenyl) stearamide

The process described in Example 3 was repeated at an increased concentration. DMF was maintained at 600 ml but the amount of 2,6-di-tert-butyl-4-nitrosophenol was increased to 164.5 g (0.7 mole). Also changed was the catalyst used. In this example 2.5 g of 3% Pt on carbon was used. The amounts of triethylamine and stearoyl chloride used were increased by a factor of 7 from that given in Example 3.

A total of 294.0 g (86%) of N(4-hydroxy-3,5-di-tert-butylphenyl) stearamide was obtained.

EXAMPLE 5

Preparation of N(4-hydroxy-3,5-di-tert-butylphenyl) stearamide

A 2 liter Parr bomb was charged with 210.5 g of 44.6% water wet (0.5 mole, pure, dry) 2,6-di-tert-butyl-4-nitrosophenol, 2.0 g of 5% Pd/C catalyst, 300 ml dichloromethane and 400 ml hexane. The nitrogen purged system was pressurized to 50 psi with hydrogen and the rate of hydrogen uptake noted. Hydrogenation was completed within one hour.

Triethylamine, 58.22 g (0.575 moles) was purged with nitrogen and under nitrogen pressure transferred into the Parr bomb at the end of the hydrogenation. Similarly was added 159.1 g (0.526 mole) of nitrogen purged stearoyl chloride. After stirring for 1 hour the dichloromethane was flushed off and heated (40° C.) mixture was transferred to a separatory funnel to separate the bottom aqueous phase. The warm organic layer was passed through a filter to remove the catalyst. The hexane solution was cooled and the product precipitated out. It was collected by filtration, washed with water and hexane and dried overnight in vacuum. Yield 209.8 g (86.2%) N(4-hydroxy-3,5-di-tert-butylphenyl) stearamide.

EXAMPLE 6

Preparation of N(4-hydroxy-3,5-di-tert-butylphenyl) acetamide

A 2 liter Parr bomb was charged with 117.5 g (0.5 mole) dry 2,6-di-tert-butyl-4-nitrosophenol, 2.0 g of 5% Pd/C catalyst and 600 ml toluene. After purging the system with nitrogen, it was pressurized to 55 psi with hydrogen. Hydrogen uptake was completed in 25 minutes.

Acetic anhydride, 56.2 g (0.55 mole) was nitrogen purged and under nitrogen pressure transferred into the Parr bomb at the end of the hydrogenation step. The mixture was stirred for one hour and then heated to 65° C. prior to removing the content from the bomb and filtering off the catalyst. The filtrate was cooled down to 5° C. and the product precipitated out.

The solid product was collected by filtration. It was washed with hexane and air dried. Obtained 120.59 g (91.75) yield. M.P. 174° C.

EXAMPLE 7

Attempted Reduction of 4-Nitro-2,6-di-tert-butylphenol (Using toluene as reaction solvent)

A 2 liter Parr bomb was charged with 25.1 g (0.1 mole) of 4-nitro-2,6-di-tert-butylphenol, 0.5 g 5% Pd/C catalyst and 400 ml toluene. The bomb was purged with nitrogen followed by a hydrogen purge. After pressuring the bomb to 62 psi with hydrogen, the content was stirred for 2 hours at 40° C. A sample was then removed and analyzed. A very small amount was reduced to the desired amine.

The content was then heated to about 80° C. and stirred under about 60 psi hydrogen for 2 hours. A sample removed from the bomb was found to contain mostly unchanged nitro starting material.

EXAMPLE 8

Reduction of 4-Nitro 2,6-di-tert-butylphenol in Methanol

A 2 liter Parr bomb was charged with 25.1 g (0.1 mole) of 4-nitro-2,6-di-tert-butylphenol, 0.65 g 5% Pd/C catalyst and 500 ml methanol. The bomb was purged with nitrogen followed by a hydrogen purge. After pressuring the bomb with hydrogen to 62 psi the stirrer was turned on with the content at room temperature.

Uptake of hydrogen was very fast indicating fast reduction of the nitro compound. Hydrogen uptake dropped to zero after 40 minutes indicating completion of reaction. The mixture was stirred for 1 hour at which time a small sample was removed. Infrared analysis indicated total conversion to the desired amine.

EXAMPLE 9

Preparation of N-Stearoyl (4-amino-2,6-di-tert-butylphenol)

The bomb containing the amine product (described in Example 8) was vented off to remove hydrogen and the system was purged with nitrogen. To the bomb was then added 10.6 g sodium carbonate in about 80 ml deaerated water. A deaerated solution of 32.75 g (7.5% excess) stearoyl chloride in 100 ml toluene was prepared and added slowly to the bomb. Stirring continued for 2 hours.

The product was isolated from the reaction mixture and crystallized from hexane yielding 230 g (47% yield). The remaining material was identified as methyl stearate which resulted from the reaction of stearoyl chloride with the solvent methanol.

What is claimed:

1. A method for making N-acylated dialkyl aminophenol, comprising the steps of:
   (a) reducing dialkyl nitrosophenol to dialkyl aminophenol by catalytic hydrogenation under catalytic conditions in an aprotic solvent reaction medium to form a reaction mixture; and
   (b) thereafter acylating the dialkyl aminophenol without isolation from said reaction mixture.

2. The method of claim 1, wherein said acylation comprises adding an acid chloride under acylating conditions.

3. The method of claim 2, wherein said acid chloride is stearoyl chloride.

4. The method of claim 1, wherein said aprotic organic solvent is selected from the group consisting of toluene, N,N-dimethylformamide, hexane, and mixtures of hexane and dichloromethane.

5. The method of claim 4, wherein said mixture of hexane and dichloromethane is in the respective weight ratio of about 1.3 to 1.0.

6. The method of claim 1, wherein said catalytic reducing conditions are oxygen-free atmosphere, temperature of from about 20° to about 50° C., and under pressure from about 50 to about 60 psi.

7. The method of claim 1 wherein the acylation reaction is performed in a nitrogen purged reaction mixture.

8. The method of claim 1, wherein said catalytic reducing agent is Pd/C.

* * * * *